(12) United States Patent
Saigal et al.

(10) Patent No.: US 7,026,513 B2
(45) Date of Patent: Apr. 11, 2006

(54) MANUFACTURE OF PHENYL ETHYLAMINE COMPOUNDS, IN PARTICULAR VENLAFAXINE

(75) Inventors: Jagdish Chand Saigal, Maharashtra (IN); Rajender Pershad Gupta, Maharashtra (IN); Vilas Vasant Pandit, Maharashtra (IN); Anand Jagannath Desai, Maharashtra (IN); Navneet Vinodrai Mehta, Maharashtra (IN); Shrikant Hambirrao Rane, Maharashtra (IN)

(73) Assignee: Nicholas Piramal India Limited, (IN)

( * ) Notice: Subject to any disclaimer, the term of this patent is extended or adjusted under 35 U.S.C. 154(b) by 0 days.

(21) Appl. No.: 10/508,930

(22) PCT Filed: Jun. 13, 2002

(86) PCT No.: PCT/IN02/00131

§ 371 (c)(1),
(2), (4) Date: Apr. 14, 2005

(87) PCT Pub. No.: WO03/080560

PCT Pub. Date: Oct. 2, 2003

(65) Prior Publication Data

US 2005/0228198 A1    Oct. 13, 2005

(30) Foreign Application Priority Data

Mar. 26, 2002   (IN) .......................... 208/MAS/2002

(51) Int. Cl.
*C07C 211/00* (2006.01)
(52) U.S. Cl. ..................................... 564/336
(58) Field of Classification Search .................. 564/336
See application file for complete search history.

(56) References Cited

U.S. PATENT DOCUMENTS

| 2,462,736 A | 2/1949 | Gresham |
| 4,535,186 A | 8/1985 | Husbands |
| 6,350,912 B1 | 2/2002 | Chavan |

OTHER PUBLICATIONS

W.E. Fristad et al., Manganese(III) gamma-Lactone Annulation with Substituted Acids, J. org. Chem., 1985, 50(17) 3143-3148.

*Primary Examiner*—Samuel Barts
(74) *Attorney, Agent, or Firm*—Pendorf & Cutliff

(57) ABSTRACT

A process for the preparation of hydroxy(cycloalkane/cyclokene) phenylethyl amine of the general formula (III) comprising alkylation of its precursor amine of general formula (II) which is in turn produced by an effective reduction process from its precursor cyanide having the general formula (I) using Raney Nickel (CORMIII) as catalyst where, either of R5 and R6 independently could be in meta or para position and R5, R6 are independently hydrogen, hydroxyl, alkyl, alkanoyloxy, cyano, nitro, alkylmercapto, amino, alkylamino, allkanamido, halo, trifluoromethyl, or taken together methylenedioxy, n is 0, 1, 2, 3, 4, R7 is hydrogen of alkyl of 1–7 carbon atom, R1 IH or alkyl of 1–3 carbon atom and R2 is alkyl 1–3 carbon atom, the dotted line represents optional unsaturation. Compounds of formulae IV, V and VI are respectively derivatives of compounds I, II and III respectively.

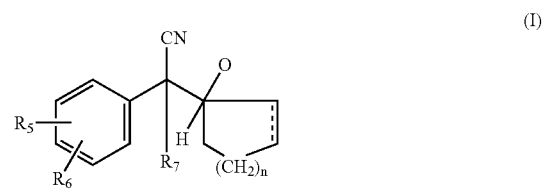

(I)

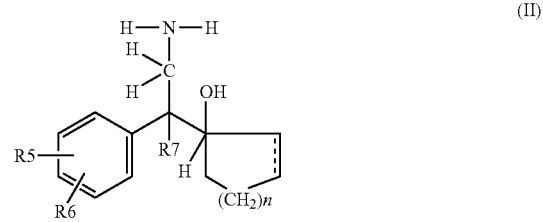

(II)

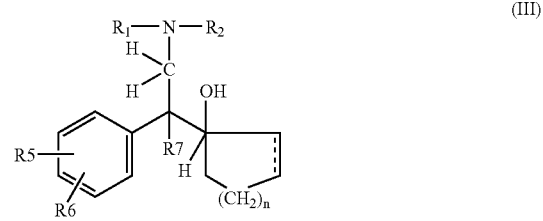

(III)

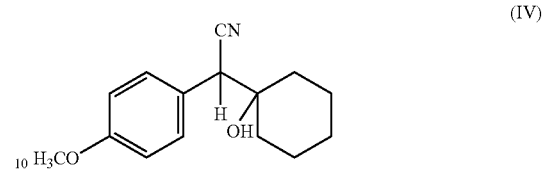

(IV)

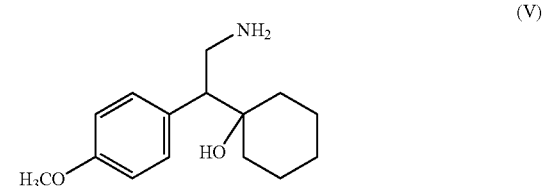

(V)

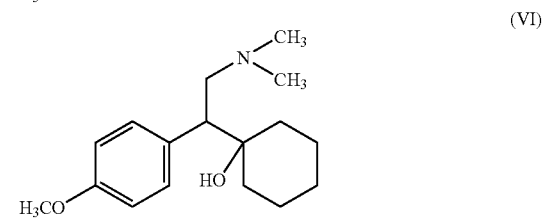

(VI)

14 Claims, No Drawings

MANUFACTURE OF PHENYL ETHYLAMINE COMPOUNDS, IN PARTICULAR VENLAFAXINE

CROSS REFERENCE TO RELATED APPLICATION

This application is a national stage of PCT/IN02/00131 filed Jun. 13, 2002 and based upon Indian Application No. 208/MAS/2002 filed Mar. 26, 2002 under the International Convention.

This invention relates to an improved process for the manufacture of hydroxy(cycloalkane or cycloalkene)phenyl ethyl amine compounds of general formula II and its derivatives and in particular the derivative of formula III. More particularly the invention relates to a process for manufacture of precursor of antidepressant of formula V, and its dialkylamino derivative of formula VI.

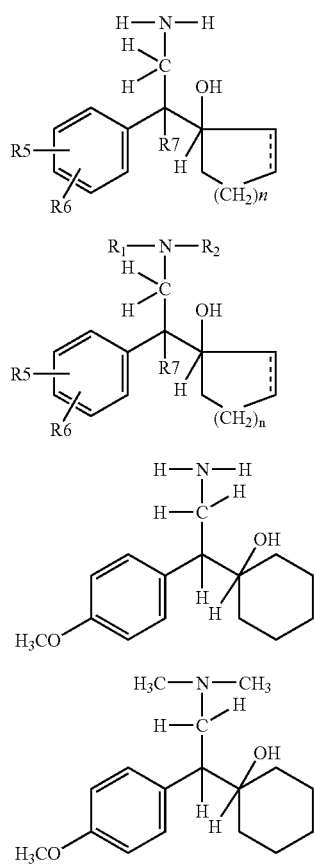

where, either of R5 and R6 independently could be in meta or para position and R5, R6 are independently hydrogen, hydroxyl, alkyl, alkoxy, alkanoyloxy, cyano, nitro, alkylmercapto, amino, alkylamino, alkanamido, halo, trifluoromethyl, or taken together methylenedioxy, n is 0, 1, 2, 3, 4; R7 is hydrogen or alkyl of 1–7 carbon atom,. R1 is H or alkyl of 1–3 carbon atom and R2 is alkyl of 1–3 carbon atom, the dotted line represents optional unsaturation.

The generic version of the antidepressants is represented as formula III and its precursor amine as formula II, and precursor of the amine of formula II is a nitrile of the compound of formula I

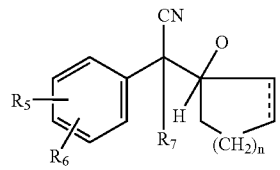

When in formula I either R5 or R6 is in para position and either one of them is —OCH3 and the other is H; R7 is hydrogen; the dotted line representing optional unsaturation is removed; and n=2 the compound of formula I is a compound of formula IV which is known as 1-[cyano-(p_methoxyphenyl)methyl]cyclohexanol.

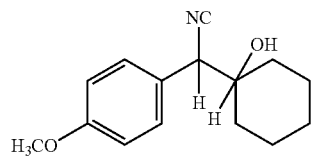

PRIOR ART

Hydroxy (cyclokene or cycloalkane)(di alkyl) amino phenyl ethyl compound has the generic formula

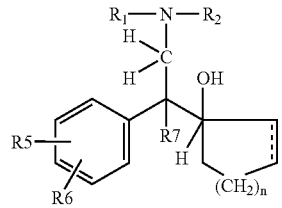

The compound of this general formula has been described in U.S. Pat. No. 4,535,186 and J. Med. Chem 33, 2809–2905

The said U.S. Pat. No. 4,535,186 and its corresponding EP 0112668A2 teaches the art of manufacture of compound of formula III from its precursor of formula II

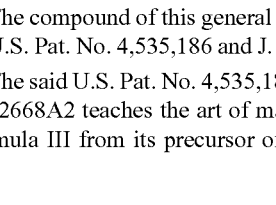

The formula II in its turn is arrived at by the reduction of a cyano compound of formula I. The overall process of synthesis of compound of formula III is as under.

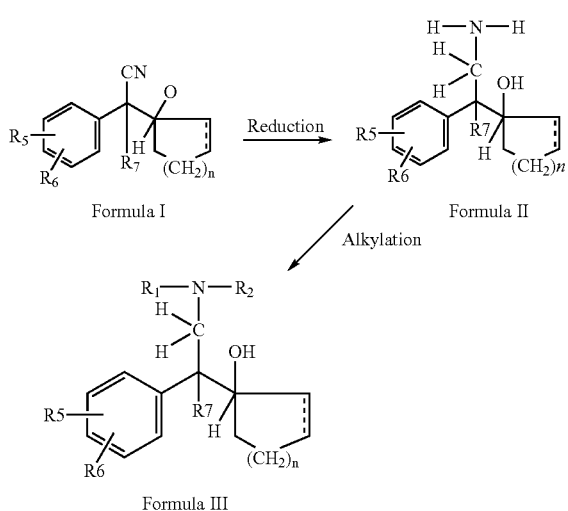

Formula I → Reduction → Formula II
Alkylation → Formula III

Reduction of the compound of formula IV gives the compound of formula V, which is chemically known as 1-[2-amino-1-(p-methoxyphenyl)ethyl]cyclohexanol.
Methylation of compound of formula V will produce the compound of formula VI which is chemically known as 1-[2-dimethyl(p-methoxyphenyl)ethyl]cyclohexanol or venlafaxine.

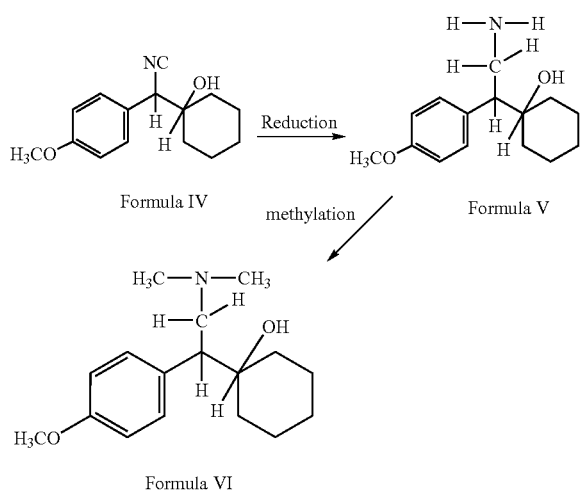

Formula IV → Reduction → Formula V
methylation → Formula VI

The reduction process is depicted as above is carried out as follows:

J. Med. Chem 33, 2809–2905; U.S. Pat. No. 4,535,186 and its corresponding EP 0112668A2 teaches the art of reduction of generic version of venlafaxine as well as venlafaxine as under
Catalyst: Raney NickelCorm III
Solvent: Methanol:Methanol ammonia (2:1)
Temp: room temp.
Pressure: 5 Kg/cm2 (72 psi)
Time 9 hrs
EP 0112669 teaches the various reduction condition as under
Pd/C (10%) and hydrogen in ethanol media
Lithium aluminium hydride in acid media
Rhodium Alumina in ammoniacal ethanol to reduce the nitrile to primary amine Yet another disclosure WO/0059851 and WO/32556 the said reduction has been carried out using CoCl2 and NaBH4.
According to Chang et al. The precursor cyano methyl compound of the formula IV can be reduced by Na BH4 and BF3 etherate to compound of formula V.
However the above process has one or other disadvantages as depicted as under.
1. Use of expensive organic catalyst like Rh/Al2O3 and BF3 etherate.
2. Use of costly reducing agent like NaBH4.
3. Most of the cases shown above the reducing agent are prone to fire hazard.

The use of Raney Ni, however, reduces the cost of reduction process as the catalyst can be recycled a number of times and hydrogen is a cheaper reducing agent.

Alkylation is performed after the preparation of the primary amine. Methylation of the primary amine is however a well established process for the preparation of dimethyl amine.

In our co-pending application No. 209/MAS/2002 there is disclosed and claimed a method for preparation of compound of formula IV which provides a higher yield compared to those described in the prior art.

The inventors have found that in the process of reduction of compound of formula IV the yield could be improved by the use of a very specific solvent system and a most effective form of catalyst combination out of a particular form of Raney Ni catalyst.

In the present system the required amine of formula V is produced at a better yield than that described in the prior art and at the same time there is provided a system which can be handled in a safer way as the system involves no hazardous chemicals and the reduction at pressure of 120 psi of hydrogen is a safer process at which the inventor carried out successful hydrogenation.

In the present invention the methylation of the amine to dimethyl amine has also been optimized.

OBJECTS

The main objective of the present invention is to produce phenyl ethyl compound of formula II and derivative thereof by an optimised process of reduction through the use of a novel solvent combination which will reduce the cyano-carbinol most effectively.

A further objective of the present invention is to provide a safe method of reduction of the cyano methyl carbinol of formula IV to amino ethyl carbinol of formula V.

It is yet another objective of the present invention to provide a method for methylating the said amine to the corresponding dimethyl derivative.

SUMMARY OF INVENTION

A process for preparation of hydroxy (cycloalkane) phenyl ethyl amine (Formula II) by reduction of cyano compound of formula 1 using Raney Nickel CORM III having bulk density between 0.40 to 0.60 gm/cc as catalyst

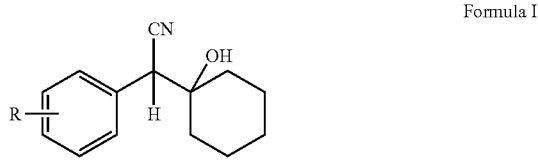

Formula I

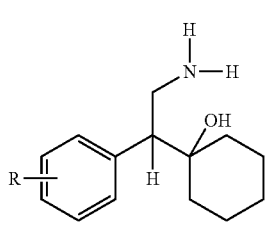

Formula II where, R is in meta or para position and independently hydrogen, hydroxyl, alkyl, alkoxy, alkanoyloxy, amino, alkyl amino, alkaneamido, halo and triflouro methyl.

DETAILED DESCRIPTION OF THE INVENTION

The invention relates to the process for safe manufacture of 1-[2-amino-1-[p-methoxyphenyl)ethyl]cyclohexanol of formula V and methylation of the compound of formula V to the compound 1-[2-dimethyl(p-methoxyphenyl)ethyl]cyclohexanol of formula VI.

In formula I when either R5 or R6 is in para position and either one of them is —OCH3 and the other is H, R7 is hydrogen; the dotted line representing optional unsaturation is removed and n=2 the compound is a compound of formula IV which is known as 1-[cyano-(p_methoxyphenyl)methyl] cyclohexanol

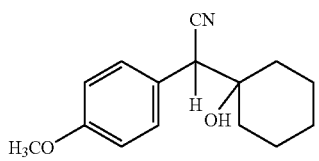

Formula IV

In formula II when either R5 or R6 is in para position and either one of them is —OCH3 and the other is H, R7 is hydrogen; the dotted line representing optional unsaturation is removed and n=2 the compound is a compound of formula V which is 1-[2-amino-1-(p-methoxyphenyl)ethyl]cyclohexanol obtained by the process of reduction of compound of formula IV

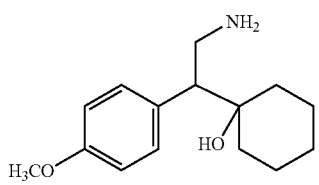

Formula V n formula I when either R5 or R6 is in para position and one of them is —OCH3 and other one is H; R1 and R2 is —CH3; R7 is H; n=2 and with optional unsaturation removed, the compound is venlafaxine of formula VI which is obtained by methylation of the compound of formula VI

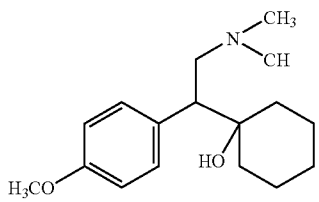

Formula VI

The reduction is carried out using Raney Ni (CORMIII) as catalyst. The reduction is carried out using a solvent media of aqueous ammonia and methanol. Preferably the combination of aqueous ammonia and methanol is in the ratio of between 1:10 to 1:1. Most preferably the ratio of aqueous ammonia to methanol is 1:5.

The catalyst is used in the proportion of 100 to 20 wt. % of the compound of formula IV. Preferably the catalyst concentration is 75% w/w of the compound of formula IV.

The compound of formula IV has a concentration in the range of 2 to 20 w/v % and preferably in the range of 7 to 13 w/v %. Most preferably the concentration is 6 w/v %.

The catalyst is aged upto 120 days after its preparation and prior to its use. Preferably the catalyst is aged for a period of between 45 to 30 days after its preparation and before its use. Most preferably, the catalyst is aged for 27 days after its preparation and before its use.

The reduction is carried out at temperature of between −5 to 40° C., preferably at 15 to 30° C. and most preferably at 27° C. The pressure is in the range of 30 to 200 psi., preferably 50 to 150 psi; and most preferably 120 psi.

The reduction is carried out for 24 hours, preferably between 8 to 24 hours and most preferably upto 9 hours.

Preferably the methylation is carried using conventional Eshweiler Clarke method.

EXAMPLE

The following process steps are provided to illustrate the invention and are non-limiting examples of the invention Reduction Catalytic reduction of compounds of formula IV gives rise to various products which are mixtures of compounds of formula V, VII and VIII. In case of venlafaxine manufacture reduction of compound IV to V various catalyst were tried and results are shown in the table I and II. It is evident from the table as well as following discussion that the reduction process is associated with various by products in different proportion. In this invention effort has been made to increase the yield of the required product V and minimise production of by products. The details discussion illustrates how the reduction as well as methylation step were optimised to get maximum yield and at the same time by products were minimised.

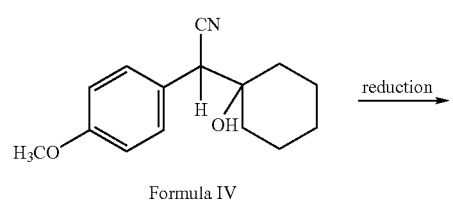

Formula IV

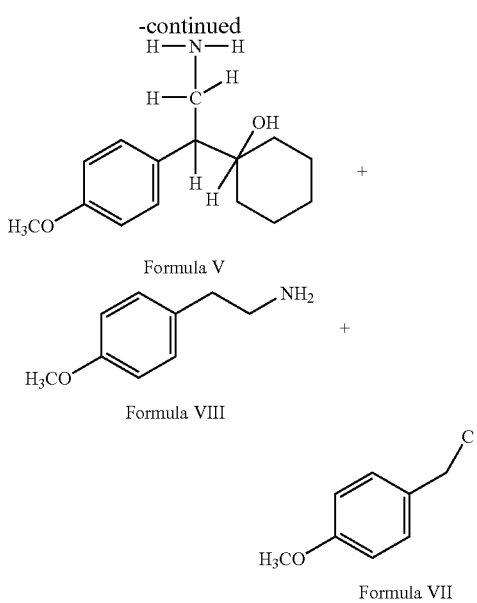

Compound (IV) on subjecting to chemical reduction using catalysts such as LAH, LAH-AlCl₃, LAH-H₂SO₄ either lead to compound (VII) by way of its retrogression or there was no reaction at all. Catalytic hydrogenation of compound (IV) using Pd/C at 35 psi and room temperature under neutral as well as acidic conditions gave the starting material back. Similarly, replacing Pd/C by Rh/Al₂O₃ and carrying out the reaction in alcoholic ammonia or acetic acid at 35 psi and room temperature did not give any product. Instead of alcoholic ammonia, when 0.1% NaOH in alcohol was used for the reaction, the reduced retrogression product (VIII) of (IV) was obtained. Finally, hydrogenation of (IV) with 30% w/w of Rh/Al₂O₃ in aq. NH₃-ethanol (1:5) at 35 psi and room temp. could give the required product (V). This compound was used as the reference sample for monitoring hydrogenation reactions using Raney Nickel as the catalyst. Catalytic hydrogenation of compound (IV) over Raney-7Ni (50–100% w/w) in alcohol or alcoholic ammonia at 45 to 95 psi and room temperature did not give any product and the starting material was recovered back. Use of 2% alcoholic NaOH or 3–5% of aq. NaOH in alcohol, in place of alcoholic ammonia, resulted in retrogression and subsequent reduction to give compound (VIII) as the sole product. Finally, with 200% w/w of the Raney Ni catalyst in aq. NH₃-EtOH (1:5) at 35 psi and room temperature, the compound (IV) could be hydrogenated to give the required product (V) in good yield (~90%).

Few more experiments were carried out to see whether lower amounts of the catalyst could be used. In one of such experiment catalyst amount was reduced to 50% w/w, the pressure was increased to 100 psi and the temperature was raised to 50° C. However, it lead to the retrogression followed by reduction and furnished the product (VIII). In another experiment, the catalyst amount taken was 100% w/w, pressure applied was 120 psi and the reaction was carried out at room temp. Interestingly, this reaction gave the required product (V) in good yields. Though, Raney Ni/H₂ system could be used successfully, the reaction always lead to the formation of varying amounts of reduced retrogression product (VIII), without an exception. In order to minimise the formation of compound (VIII) during the reduction of compound (IV), few more parameters were studied in greater detail. The results are summarised below (Table-III).

The pressure of the reaction was fixed at 120 psi, as that was the upper limit of the pressure available for the scale-up studies in India. Three varieties of Raney Ni catalyst were studied such as Raney Ni-type B, Raney Ni-type F and Raney Ni type CORM-III. A reaction with Raney Ni-type B was very slow and did not go to completion even after 24 hrs. The product formed was the mixture of compound (V) and compound (VII), the former being the major and the latter as minor one. Raney Ni-type F caused complete retrogression and gave the reduced product (VIII). A reaction with Raney Ni CORM-III type could go to completion in 8–9 hrs and formed compound (V) as the major product and compound (VIII) as the minor impurity. Encouraged by such an observation, Raney Ni CORM-III type was selected as the catalyst for further studies. Three different catalyst amounts such as 100% w/w, 75% w/w and 50% w/w were studied and it was found that 50% w/w catalyst required 16 hrs for the completion of the reaction, whereas, 75% w/w and 100% w/w catalysts could bring about the reaction to completion in 8–9 hrs. Therefore, 75% w/w amount of the catalyst was taken for further studies. The substrate concentration was studied from 1.6% w/v to 12% w/v and it was found that upto 6% w/v substrate concentration the retrogression is minimum and thereafter the amount of the retrogression product goes on increasing. The reaction goes smooth at 27° C., the rise in temperature leads to retrogression and at 50° C. the reaction gives only the retrogression product (VIII). Raney Nickel catalyst is usually accompanied with a base (NaOH). The traces of base present during hydrogenation, at high pressure, leads to the retrogression. Therefore, the catalyst needs to be washed thoroughly with water before use. Washing the catalyst with 5% acetic acid followed by water did not significantly reduced the concentration of the retrogression product (VIII).

Therefore, washing of the catalyst with excess water was considered to be sufficient to remove the traces of alkali present with the catalyst. The age of the catalyst was also found to play some role in the formation of retrogression product (VIII). The catalyst of the age of three weeks and above gave minimum amount of the retrogression product. Finally, in the optimised conditions, 75% w/w Raney Ni CORM-III catalyst with 3 weeks aging was used after repeated washings with water at 6% w/w substrate conc. In aqueous ammonia-methanol solvent maintained at 27° C. under 120 psi Hydrogen pressure for 8–9 hrs. The yield of the product under these conditions was about 90% and contained about 89% of the required product (V) and 11% of the retrogression product (VIII). The impurity, VIII, was removed in the subsequent step.

Step-3: Methylation

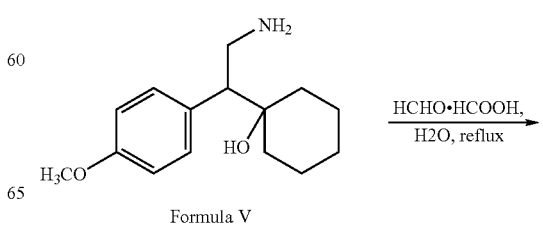

-continued

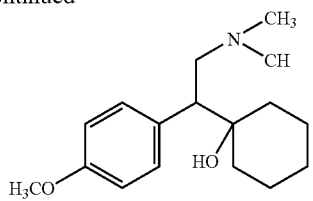

Formula VI

After the successful reduction of the nitrile function to the amino group, the next task was to carry out the methylation of the amino function. As per the literature, such a conversion can be carried out using Eshwieler Clarke conditions. In the present case we also carried on the same Eshwieler Clarke reaction for converting compound (V) to compound (VI). In a typical experiment compound (V) was refluxed with formaldehyde, formic acid and water for about 16 hrs. After the work-up the methylated product was directly treated with IPA.HCl The hydrochloride salt of Venlafaxine was precipitated out whereas, the hydrochloride salt of the reduced retrogression product (VIII) remained in the solution. The final product was well characterized from its spectral data, m.p. and HPLC.

Certain modifications were tried in this step in view of optimizing the yields. In one of the modifications, sodium formate was added to the Eshwieler Clarke reaction mixture. It is supposed to minimize the formylation of amine and thereby increase the yield of the required product. However, in the present case it did not significantly increase the yield of the reaction. In another modification the sequence of addition of formaldehyde and formic acid was reversed. However, this lead to the decrease in yield. In yet another modification, the reaction time was varied from 16 to 18 hrs or 30 hrs. However, in both case there was no increase in the product yield.

Mass Spectra Analysis:
Molecular weight: 249 [(M+1)$^+$ by C.I.M.S.]

TABLE I

Results of Condensation Reaction for cyano carbinol

| Sr. No. | Expt. No. | Mol ratio (2/1) | Base (equiv.) | Catalyst (equiv.) | Solvent | Temp. (° C.) | Time (hrs.) | Yield (%) |
|---|---|---|---|---|---|---|---|---|
| 1 | VDG/00/01 | 1.05 | n-BuLi | — | THF | −78 | 3 | 82 |
| 2 | VDG/00/02 | 1.10 | n-BuLi | — | THF | −30 | 3 | 72 |
| 3 | VDG/00/03 | 1.10 | n-BuLi | — | THF | −5 | — | — |
| 4 | VDG/00/04 | 1.00 | NaNH$_2$ | — | THF | −78 | 3 | 62 |
| 5 | VDG/00/05 | 1.00 | NaNH$_2$ | — | THF | −5 | 2 | 30 |
| 6 | VDG/00/06 | 1.00 | 50% NaOH | TEBAB | H$_2$O | 27 | 3 | Very Poor |
| 7 | VDG/00/07 | 1.00 | 50% NaOH | Cetrimide | H$_2$O | 27 | 3 | Very Poor |
| 8 | VDG/00/08 | 1.00 | 50% NaOH | TBAB | H$_2$O | 27 | 3 | Very Poor |
| 9 | VDG/00/09 | 1.10 | 10% NaOH (0.46 eq.) | TBAB (0.002 eq.) | H$_2$O | 27 | 3–4 | 82 |
| 10 | VDG/00/10 | 1.10 | 10% NaOH (0.46 eq.) | TBAB (0.002 eq.) | H$_2$O | 27 | 8 | 82 |
| 11 | VDG/00/11 | 1.30 | 10% NaOH (0.46 eq.) | TBAB (0.002 eq.) | H$_2$O | 27 | 8 | 90 |
| 12 | VDG/00/12 | 1.35 | 10% NaOH (0.46 eq.) | TBAB (0.002 eq.) | H$_2$O | 27 | 8 | 90 |
| 13 | VDG/00/13 | 1.50 | 10% NaOH (0.46 eq.) | TBAB (0.002 eq.) | H$_2$O | 27 | 8 | 83 |
| 14 | VDG/00/14 | 1.40 | 10% NaOH (1.0 eq.) | TBAB (0.002 eq.) | H$_2$O | 27 | 3 | 92 |
| 15 | VDG/00/15 | 1.10 | 10% NaOH (0.46 eq.) | TBAB (0.001 eq.) | H$_2$O | 27 | 3 | 92 |
| 16 | VDG/00/16 | 1.40 | 10% NaOH (0.46 eq.) | TBAB (0.002 eq.) | H$_2$O | 18 | 6 | 91 |
| 17 | VDG/00/17 | 1.35 | 10% NaOH (0.46 eq.) | TBAB (0.002 eq.) | H$_2$O | 18 | 6 | 91 |
| 18 | VDG/00/18 | 1.35 | 10% NaOH (1.0 eq.) | TBAB (0.002 eq.) | H$_2$O | 15 | 3 | 92 |

TABLE II

Reduction of Compd. (IV) using different catalysts

| Sr. No. | Expt. No. | Catalyst (% w/w) | Solvent | Concn. (% w/v) | P (psi) | Temp. (° C.) | Time (hrs.) | Product |
|---|---|---|---|---|---|---|---|---|
| 1 | VDG/00/19 | LAH | THF | — | — | RT | 15 | 1 |
| 2 | VDG/00/20 | LAH—AlCl$_3$ | Ether | — | — | RT | 15 | 1 |
| 3 | VDG/00/21 | LAH—H$_2$SO$_4$ | THF | — | — | 0 | 4 | Nil |
| 4 | VDG/00/22 | H$_2$/5% Pd—C (20) | MeOH | — | — | RT | 15 | Nil |
| 5 | VDG/00/23 | H$_2$/5% Pd—C (20) | Dioxane | — | 35 | RT | 4 | Nil |
| 6 | VDG/00/24 | H$_2$/10% Pd—C (20) | IPA—AcOH | — | 35 | RT | 4 | Nil |
| 7 | VDG/00/25 | H$_2$/10% Pd—C (20) | IPA.HCl | — | 35 | RT | 4 | Nil |
| 8 | VDG/00/26 | H$_2$/10% Pd—C (35) | AcOH | — | 35 | RT | 4 | Nil |
| 9 | VDG/00/27 | H$_2$/Rh—Al$_2$O$_3$ (20) | Methanolic NH$_3$ | — | 35 | RT | 4 | Nil |
| 10 | VDG/00/28 | H$_2$/Rh—Al$_2$O$_3$ (43) | Ethanolic NH$_3$ | — | 35 | RT | 3 | Nil |
| 11 | VDG/00/29 | H$_2$/Rh—Al$_2$O$_3$ (25) | 0.1% NaOH—EtOH | — | 35 | RT | 3 | 8 |
| 12 | VDG/00/30 | H$_2$/Rh—Al$_2$O$_3$ (20) | 10% NaOH—EtOH | — | 35 | RT | 3 | 8 |
| 13 | VDG/00/31 | H$_2$/Rh—Al$_2$O$_3$ (20) | AcOH | — | 35 | RT | 3 | Nil |
| 14 | VDG/00/32 | H$_2$/Rh—Al$_2$O$_3$ (30) | Aq. NH$_3$—MeOH (1:5) | — | 35 | RT | 9 | 4 |
| 15 | VDG/00/33 | H$_2$/Rh—Al$_2$O$_3$ (100) | Aq. NH$_3$—MeOH (1:5) | — | 35 | RT | 9 | 4 |
| 16 | VDG/00/34 | H$_2$/Rh—Al$_2$O$_3$ (70) | Aq. NH$_3$—MeOH (1:5) | — | 35 | RT | 9 | 4 |
| 17 | VDG/00/35 | H$_2$/Raney Ni (10) | Methanolic NH$_3$ | — | 45 | RT | 2 | Nil |
| 18 | VDG/00/36 | H$_2$/Raney Ni (10) | Methanolic NH$_3$ | — | 95 | RT | 3 | Nil |
| 19 | VDG/00/37 | H$_2$/Raney Ni (30) | Methanolic NH$_3$ | — | 45 | RT | 4 | Nil |
| 20 | VDG/00/38 | H$_2$/Raney Ni (30) | Methanolic NH$_3$ | — | 45 | RT | 10 | Nil |

TABLE II-continued

Reduction of Compd. (IV) using different catalysts

| Sr. No. | Expt. No. | Catalyst (% w/w) | Solvent | Concn. (% w/v) | P (psi) | Temp. (° C.) | Time (hrs.) | Product |
|---|---|---|---|---|---|---|---|---|
| 21 | VDG/00/39 | H$_2$/Raney Ni (100) | 5% NaOH—MeOH | — | 35 | RT | 1.5 | 8 |
| 22 | VDG/00/40 | H$_2$/Raney Ni (50) | 5% NaOH—MeOH | — | 35 | RT | 2.5 | 8 |
| 23 | VDG/00/41 | H$_2$/Raney Ni (50) | 3% NaOH—MeOH | — | 35 | RT | 2.5 | 8 |
| 24 | VDG/00/42 | H$_2$/Raney Ni (100) | MeOH | — | 35 | RT | 2.5 | Nil |
| 25 | VDG/00/43 | H$_2$/Raney Ni (50) | 2% Ethanolic NaOH | — | 35 | RT | 2.5 | 8 |
| 26 | VDG/00/44 | H$_2$/Raney Ni (25) | 2% Ethanolic NaOH | — | 35 | RT | 2.5 | 8 |
| 27 | VDG/00/45 | H$_2$/Raney Ni (50) | Ethanolic NH$_3$ | — | 120 | 50 | 10 | 8 |
| 28 | VDG/00/46 | H$_2$/Raney Ni (50) | Aq. NH$_3$—EtOH (1:5) | — | 100 | 50 | 8 | 8 |
| 29 | VDG/00/47 | H$_2$/Raney Ni (200) | Aq. NH$_3$—EtOH (1:5) | 2.0 | 35 | RT | 18 | 4 |
| 30 | VDG/00/48 | H$_2$/Raney Ni (100) | Aq. NH$_3$—EtOH (1:5) | 1.6 | 120 | RT | 8 | 4 |
| 31 | VDG/00/49 | H$_2$/Raney Ni (50) | Aq. NH$_3$—EtOH (1:5) | 6.0 | 225 | RT | 8 | 4 |
| 32 | VDG/00/50 | H$_2$/Raney Ni (25) | Aq. NH$_3$—EtOH (1:5) | 6.0 | 225 | RT | 13 | 4 |

TABLE III

Reduction of compound (IV) using Raney Ni (CORM III) in aq. NH$_3$-alcohol (1:5) at 120 psi

| Sr. No. | Expt. No. | Batch size (g.) | Solvent | Conc. (% w/v) | Cat. Amt. (% w/w) | Cat. Age (days) | Temp. (° C.) | Time (hrs.) | Crude pdt. (% Yield) | Product V (%) | Impurity VIII (%) |
|---|---|---|---|---|---|---|---|---|---|---|---|
| 1 | VDG/00/51 | 5 | Aq.NH$_3$—EtOH (1:4) | 1.6 | 100 | 5 | 27 | 8 | 94 | 84 | 16 |
| 2 | VDG/00/52 | 21 | Aq.NH$_3$—EtOH (1:4) | 7 | 47.6 | 33 | 27 | 15 | 74 | 78 | 22 |
| 3 | VDG/00/53 | 1800 | Aq.NH$_3$—EtOH (1:4) | 12 | 75 | 39 | 27 | 12 | — | 28 | 72 |
| 4 | VDG/00/54 | 72 | Aq.NH$_3$—MeOH (1:4) | 12 | 75 | 69 | 27 | 10 | 88 | 85 | 15 |
| 5 | VDG/00/55 | 72 | Aq.NH$_3$—MeOH (1:4) | 12 | 75 | 70 | 27 | 12 | 88 | 86 | 14 |
| 6 | VDG/00/56 | 180 | Aq.NH$_3$—MeOH (1:4) | 6 | 75 | 110 | 25 | 12 | 84 | 82 | 18 |
| 7 | VDG/00/57 | 72 | Aq.NH$_3$—MeOH (1:4) | 12 | 75 | 21 | 27 | 11 | 90 | 38 | 62 |
| 8 | VDG/00/58 | 180 | Aq.NH$_3$—MeOH (1:4) | 6 | 75 | 25 | 27 | 10 | 89 | 89 | 11 |
| 9 | VDG/00/59 | 72 | Aq.NH$_3$—MeOH (1:4) | 6 | 75 | 28 | 27 | 12 | 91 | 82 | 18 |
| 10 | VDG/00/60 | 36 | Aq.NH$_3$—MeOH (1:4) | 6 | 75 | 68 | 30 | 10 | 75 | 75 | 25 |
| 11 | VDG/00/61 | 36 | Aq.NH$_3$—MeOH (1:4) | 6 | 75 | 70 | 30 | 10 | 85 | 80 | 20 |
| 12 | VDG/00/62 | 36 | Aq.NH$_3$—MeOH (1:4) | 6 | 75 | 75 | 24 | 12 | — | 87 | 13 |

The invention claimed is:

1. A process for preparation of hydroxy (cycloalkane) phenyl ethyl amine (Formula II) comprising reducing a cyano compound of formula 1 using Raney Nickel CORM III having bulk density between 0.40 to 0.60 gm/cc as catalyst

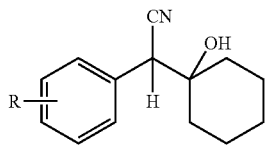

Formula I

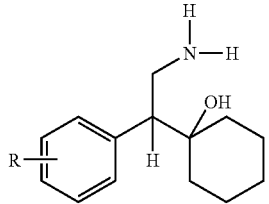

Formula II where, R is in meta or para position and independently hydrogen, hydroxyl, alkyl, alkoxy, alkanoyloxy, amino, alkyl amino, alkaneamido, halo or trifluoro methyl.

2. The process according to claim 1, wherein the said Raney Nickel has a particle size of 40 to 50 μm.

3. The process according to claim 1, wherein said Raney Nickel comprises 86 to 88 wt % Nickel and 8 to 10 wt % Aluminum.

4. The process according to claim 1, wherein said Raney Nickel has nitrobenzene activity between 55–65 ml./gm./min of Hydrogen.

5. The process according to claim 1, wherein said Raney Nickel has susceptibility to dehalogenation less than 1%.

6. The process according to claim 1, wherein R is in para position and is —OCH$_3$ and the compound of formula 1 is 1-[cyano-(p-methoxyphenyl)methyl]cyclohexanol, a compound of formula III:

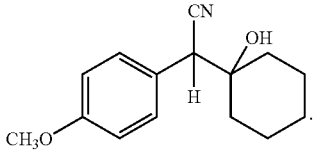

Formula III

7. The process according to claim 1, wherein said reduction is carried out in solvent of aqueous ammonia and methanol.

8. The process according to claim 1, wherein said reduction is carried out at temperature between −5 to 40° C.

9. The process according to claim 8, wherein said temperature is between 15 to 30° C.

10. The process according to claim 9, wherein said temperature is 27° C.

11. The process according to claim 1, wherein said reduction is carried out for a period of up to about 24 hours.

12. The process according to claim 11, wherein said reduction is carried out for a period of 8 to 24 hours.

13. The process according to claim 12, wherein said reduction is carried out for a period of 9 hours.

14. The process according to claim 1, wherein said reduction is carried out at a pressure of 120 psi of hydrogen.

* * * * *